(12) United States Patent
Fukuchi et al.

(10) Patent No.: US 9,228,872 B2
(45) Date of Patent: Jan. 5, 2016

(54) PARTICLE PHOTOGRAPHING DEVICE AND FLOW VELOCITY MEASUREMENT DEVICE

(71) Applicant: HONDA MOTOR CO., LTD., Tokyo (JP)

(72) Inventors: Yuichi Fukuchi, Saitama (JP); Masato Nakajima, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 0 days.

(21) Appl. No.: 14/557,626

(22) Filed: Dec. 2, 2014

(65) Prior Publication Data

US 2015/0177041 A1    Jun. 25, 2015

(30) Foreign Application Priority Data

Dec. 25, 2013    (JP) ................. 2013-268011

(51) Int. Cl.
*G01P 3/36* (2006.01)
*G01F 1/704* (2006.01)
*G01N 15/14* (2006.01)
*G01N 15/10* (2006.01)
*G01N 15/00* (2006.01)

(52) U.S. Cl.
CPC ............ *G01F 1/704* (2013.01); *G01N 15/1436* (2013.01); *G01N 15/1463* (2013.01); *G01N 2015/0046* (2013.01); *G01N 2015/0053* (2013.01); *G01N 2015/1075* (2013.01); *G01P 3/36* (2013.01)

(58) Field of Classification Search
CPC . G01N 21/645; G01N 15/1434; G01N 21/01; G01N 1/10; G01N 21/6458; G01N 2201/062; G01N 2201/0846; G01N 27/44721; G01N 15/1436; G01N 15/147; G01N 15/1484; G01N 2015/1006; G01N 21/1702
See application file for complete search history.

(56) References Cited

U.S. PATENT DOCUMENTS

| | | | | |
|---|---|---|---|---|
| 4,659,218 A | * | 4/1987 | de Lasa | B01J 8/1809 250/227.29 |
| 4,871,251 A | * | 10/1989 | Preikschat | G01N 15/0205 356/336 |
| 5,953,120 A | * | 9/1999 | Hencken | G01N 21/53 356/338 |
| 6,396,979 B1 | * | 5/2002 | Freud | G01N 15/0205 385/15 |
| 2003/0123051 A1 | * | 7/2003 | McGrew | B82Y 10/00 356/72 |
| 2003/0133112 A1 | * | 7/2003 | Tsutsui | G01N 21/474 356/338 |
| 2004/0038413 A1 | * | 2/2004 | Kramer | G01N 15/1031 436/63 |
| 2007/0162095 A1 | * | 7/2007 | Kimmel | A61B 1/00089 600/109 |
| 2008/0058647 A1 | * | 3/2008 | Kruger | A61B 5/0261 600/454 |
| 2009/0021734 A1 | * | 1/2009 | Shiba | G01N 15/0205 356/336 |
| 2009/0147373 A1 | * | 6/2009 | Rolland | A61B 5/0066 359/665 |
| 2010/0220315 A1 | * | 9/2010 | Morrell | G01N 15/1459 356/73 |
| 2010/0228123 A1 | * | 9/2010 | Brennan | A61B 5/0066 600/437 |

FOREIGN PATENT DOCUMENTS

JP    2010-101881 A    5/2010

* cited by examiner

*Primary Examiner* — Michael P Stafira
(74) *Attorney, Agent, or Firm* — Squire Patton Boggs (US) LLP

(57) ABSTRACT

A particle photographing device 2 includes: an illumination optical system 13 that illuminates particles with sheet-like illumination light based on laser light from an end of an optical fiber 7; an imaging portion 6 that images the illuminated particles; and a regulation portion 14 that changes the distance between the end of the optical fiber 7 and the illumination optical system 13.

6 Claims, 4 Drawing Sheets

PARTICLE PHOTOGRAPHING DEVICE AND FLOW VELOCITY MEASUREMENT DEVICE

BACKGROUND OF THE INVENTION

1. Field of the Invention

The present invention relates to a particle photographing device that photographs particles dispersed in a fluid, and a flow velocity measurement device that measures a flow velocity distribution in the fluid using the particle photographing device.

2. Description of the Related Art

A flow velocity measurement device that photographs tracer particles dispersed in a fluid using a particle photographing device, acquires the amount of movement of a tracer particle group based on the imaging data, and measures a flow velocity distribution in the fluid based on the amount of movement has been conventionally known (for example, see Patent Document 1).

The particle photographing device described in Patent Document 1 includes: a probe portion placed in a fluid in which particles are dispersed; an optical fiber that introduces laser light into the probe portion; and an imaging portion that images the particles in the fluid illuminated based on the laser light. The probe portion includes an illumination optical system that illuminates the particles in the fluid based on illumination light generated by diffusing, by a diffuser plate, the laser light emitted from an end position of the optical fiber. In the particle photographing device in Patent Document 1, a slit formed in the probe portion limits the photographing range of the fluid to a band-like area.

However, since the illumination light for illuminating the particles is generated by diffusing the laser light by the diffuser plate, the energy of the laser light available for illumination is lost to some extent by the diffuser plate. The particle photographing device in Patent Document 1 thus has the drawback of low illuminance of illumination light, as compared with a particle photographing device using no diffuser plate.

On the other hand, in measurement of a velocity distribution in a fluid by typical particle image velocimetry (PIV), laser light output from one end of an optical fiber is formed into sheet-like light having an appropriate thickness by an illumination optical system including a plurality of lenses, and the range illuminated by the sheet-like light is photographed. By limiting the photographing range of the fluid to a band-like area in this way, the velocity distribution can be measured accurately.

CITATION LIST

Patent Literature

Patent Document 1: Japanese Patent Application Laid-Open No. 2010-101881

SUMMARY OF THE INVENTION

The above-mentioned illumination optical system for forming the laser light into the sheet-like light is advantageous if a wider measurable range having a thickness suitable for the measurement with the sheet-like light can be secured and also the measurable range can be changed in the optical axis direction. The illumination optical system is therefore composed of an optical system that includes four or more lenses including large-size lenses and has a variable focal length. Such an illumination optical system occupies a considerably large volume in the probe portion.

When the probe portion is placed in the fluid to be measured, the large illumination optical system may significantly disturb the flow field of the fluid. This leads to a failure to accurately measure the velocity distribution in the fluid. Besides, in the case of measuring the velocity distribution in a narrow area, the large illumination optical system may obstruct and the placement of the probe portion may become difficult.

Moreover, in particle image velocimetry (PIV) using illumination light generated by forming laser light from an optical fiber into a sheet-like form, the quantity of illumination light tends to be insufficient in the case where sheet-like illumination light appropriately focused in the photographing range cannot be obtained. The insufficient quantity of light is likely to cause noise in image data obtained as a result of imaging by the imaging portion. This makes it difficult to specify the positions of the particles with high precision, and hampers accurate velocity distribution measurement.

In view of the problems of the conventional techniques stated above, the present invention has an object of providing a particle photographing device that has a compact illumination optical system and is capable of photographing with sufficient quantity of illumination light as much as possible, and a flow velocity measurement device using the particle photographing device.

A particle photographing device according to the present invention includes: a probe portion placed in a fluid in which particles are dispersed; an optical fiber that emits laser light from an end portion thereof; and an imaging portion that images the particles illuminated based on the laser light emitted from the end portion of the optical fiber, wherein the probe portion includes: an illumination optical system that illuminates the particles with sheet-like illumination light based on the laser light emitted from the end portion of the optical fiber; and a regulation portion that regulates a focusing position of the laser light by the illumination optical system, by changing a distance between the end portion of the optical fiber and the illumination optical system.

According to the present invention, the distance between the end portion of the fiber and the illumination optical system is changed to regulate the focusing position of the laser light, i.e. the thickness of the sheet-like light. Therefore, the position of illumination by the illumination light can be regulated without changing the focal length of the illumination optical system. This ensures an appropriate illumination position for the imaging range of the imaging portion, and allows the particles to be photographed with high precision.

Since there is no need to change the focal length of the illumination optical system in order to regulate the focusing position, the illumination optical system does not need to include several or more large-size lenses for enabling focal length regulation. Accordingly, the number and size of lenses in the illumination optical system can be reduced, making the illumination optical system more compact. Moreover, a smaller number of lenses allow the particles to be photographed with a larger light quantity of illumination light.

In the present invention, the particle photographing device may include a laser device that supplies the laser light introduced into the probe portion, to the optical fiber, wherein the regulation portion regulates the focusing position of the laser light by setting a position of the end portion of the optical fiber to become farther from the illumination optical system when an output set value of the laser light in the laser device is increased and to become closer to the illumination optical system when the output set value is decreased, to enable the illumination optical system to accurately illuminate an imaging range of the imaging portion regardless of a change of the output set value.

It is known that the spread angle of laser light emitted from one end of an optical fiber changes with a change in laser light output value of a laser device that supplies the laser light. When the spread angle of the laser light changes, the focusing position of the laser light by the illumination optical system changes, too.

Accordingly, in the present invention, the focusing position of the laser light is regulated in response to the change in spread angle of the laser light in the above-mentioned manner so that the illumination optical system accurately illuminates the imaging range of the imaging portion. As a result, the laser light is focused on the appropriate position regardless of the change of the laser light output value, and so the particles can be photographed with high precision using a sufficient quantity of illumination light free of degradation.

In the present invention, the regulation portion may include: a motor that changes the distance between the end portion of the optical fiber and the illumination optical system; and a motor controller that controls the motor, and the motor controller may regulate the focusing position via the motor. By automatically regulating the focusing position in this way, the particles can be always photographed with high precision.

In the present invention, the probe portion may include a housing that houses the illumination optical system, the housing may have a front end surface provided with a flat transparent plate through which the illumination light from the illumination optical system passes, and an outer plate surface of the transparent plate in the front end surface and other part of the front end surface except the outer plate surface of the transparent plate may be positioned coplanar or the outer plate surface of the transparent plate may protrude from the other part where the protrusion amount is not greater than a predetermined value.

In the case where the probe portion is placed in a flowing gas in which oil droplet particles are dispersed, there is a possibility that the oil droplet particles adhere to the transparent plate and interferes with the passage of the illumination light or refracts the illumination light. In view of this, in the present invention, the front end surface of the housing is formed of one plane including the portion of the transparent plate, or the protrusion amount of the plate surface of the transparent plate in the front end surface is not greater than the predetermined amount.

The predetermined amount is set so that, even in the case where the oil droplet particles adhere to the transparent plate, the particles are easily removed from the transparent plate by gas flow. The above-mentioned defects caused by the oil droplet particles adhering to the transparent plate can therefore be prevented.

In the present invention, the housing may contain the regulation portion in a rear side of the illumination optical system, and have a back end surface at an opposite side of the front end surface, the regulation portion may include: a movable portion to which the end portion of the optical fiber is fixed, and that is movably guided in an optical axis direction of the illumination optical system; and a drive screw that is screwed with the movable portion to change a position of the movable portion in the optical axis direction, and a part of the movable portion to which the optical fiber is fixed and a head of the drive screw may protrude from the back end surface.

Thus, both the head of the drive screw in the regulation portion which needs to protrude to the outside of the housing and the part of the movable portion to which the optical fiber is fixed protrude from the back end surface. The liquid including the particles adhering to the front end surface of the housing is accordingly prevented from coming around to the head of the drive screw or the part to which the optical fiber is fixed, as much as possible. Hence, the drive screw and the optical fiber can be kept from stains and other adverse effects or the like by the liquid.

A flow velocity measurement device according to the present invention includes: the particle photographing device described above; and a computer that obtains a flow velocity distribution in a fluid, based on imaging data of tracer particles in the fluid obtained by the particle photographing device. With this structure, the flow velocity distribution in the fluid can be measured while benefiting from the above-mentioned advantageous effects of the particle photographing device.

DESCRIPTION OF THE PREFERRED EMBODIMENTS

Figure 1:
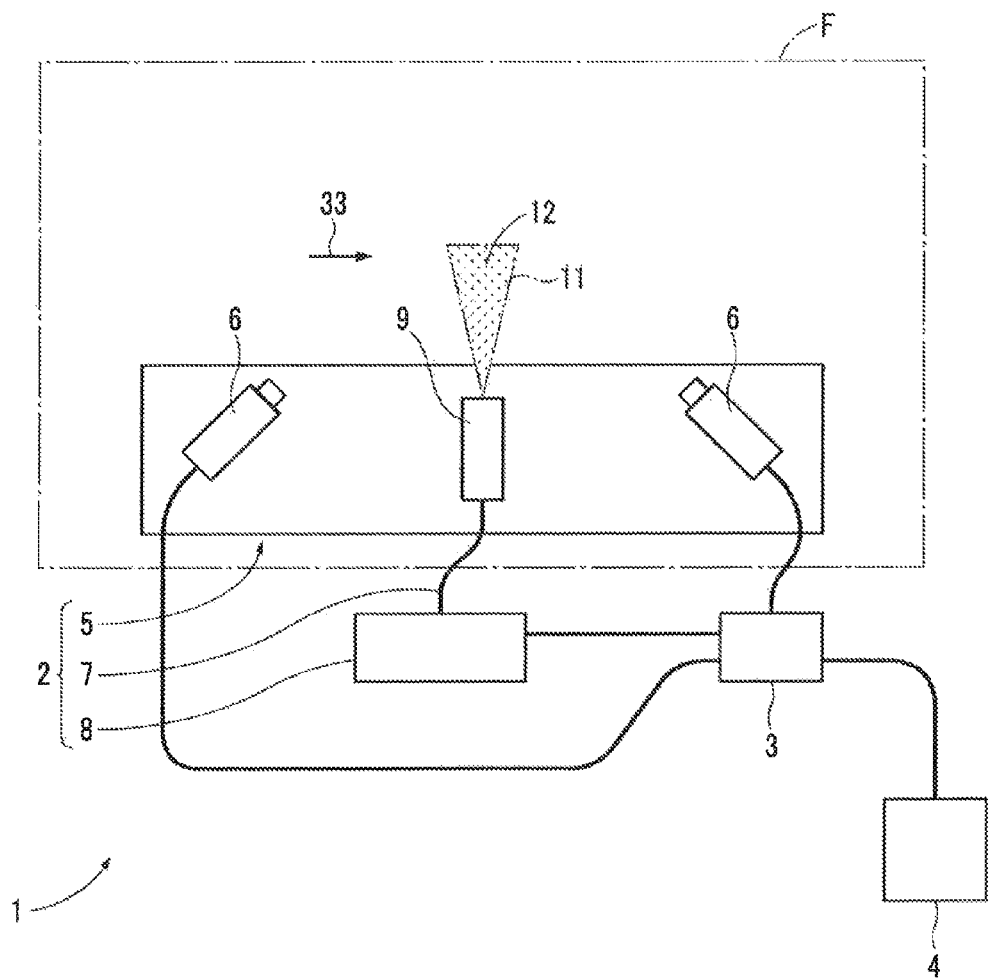
FIG. 1 is a top view showing a situation where a velocity distribution in a flow field is measured by a flow velocity measurement device according to an embodiment of the present invention.

The following describes embodiments of the present invention with reference to attached drawings. As shown in FIG. 1, a flow velocity measurement device 1 in an embodiment includes: a particle photographing device 2 that photographs tracer particles moving in a flow field F; a computer 3 connected to the particle photographing device 2; and a timing control device 4 connected to the particle photographing device 2 and the computer 3. For example, the flow field F is formed by air flowing in a wind tunnel. The tracer particles are liquid particles such as aquatic liquid particles or oil particles supplied from a seeding device not shown.

The computer 3 computes the velocity distribution in the flow field F by particle image velocimetry (PIV), based on image data from the particle photographing device 2. For example, the computer 3 acquires the amount of movement of the tracer particles in a very short time, based on image data of the tracer particles in the flow field F acquired by the particle photographing device 2. The computer 3 calculates the velocity distribution in the flow field F, based on the acquired amount of movement of the tracer particles.

The particle photographing device 2 includes: a probe portion 5 placed in the fluid of the flow field F in which the tracer particles are dispersed; an optical fiber 7 that introduces laser light for illuminating the tracer particles; and a laser device 8 that supplies the laser light to the optical fiber 7.

The probe portion 5 includes: an illumination portion 9 that illuminates the tracer particles in the flow field F; and imaging portions 6 that images the tracer particles illuminated by the illumination portion 9. Though the probe portion 5 includes two imaging portions 6 in this example, the number of imaging portions 6 may be one, or three or more.

The timing control device 4 is connected to the laser device 8 and the imaging portions 6 via the computer 3, and controls the timing of light emission by the laser device 8, the timing of imaging by the imaging portions 6, and the timing of acquiring image data from the imaging portions 6 by the computer 3.

Figure 2A:
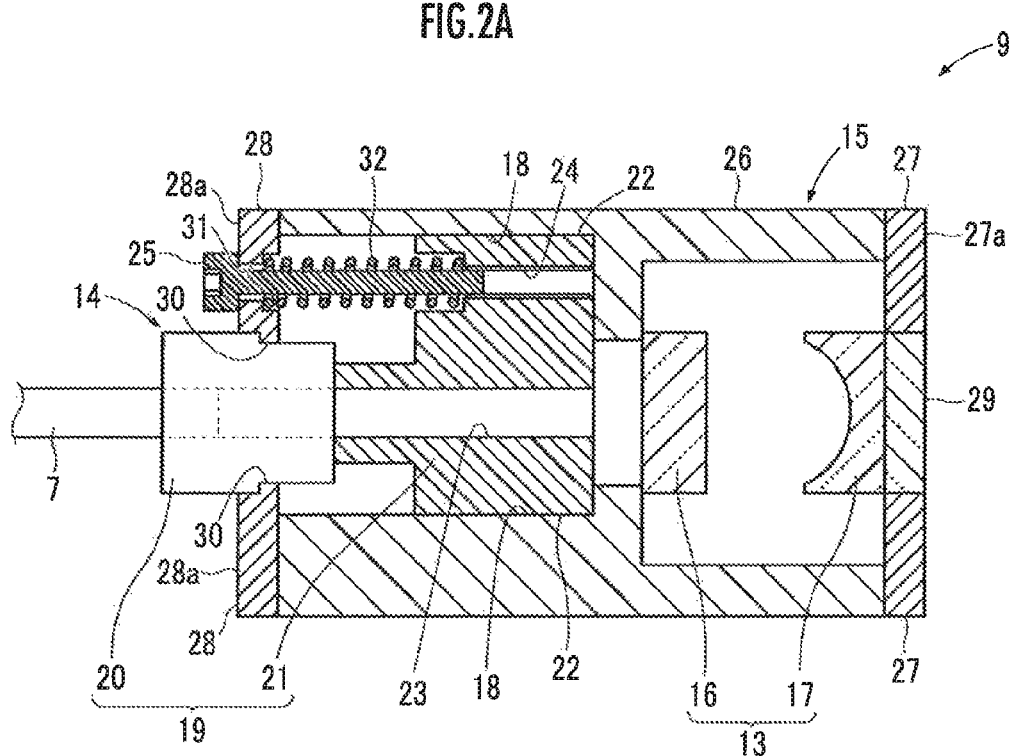
FIG. 2A is a top sectional view of an illumination portion in the flow velocity measurement device in FIG. 1.
Figure 2B:
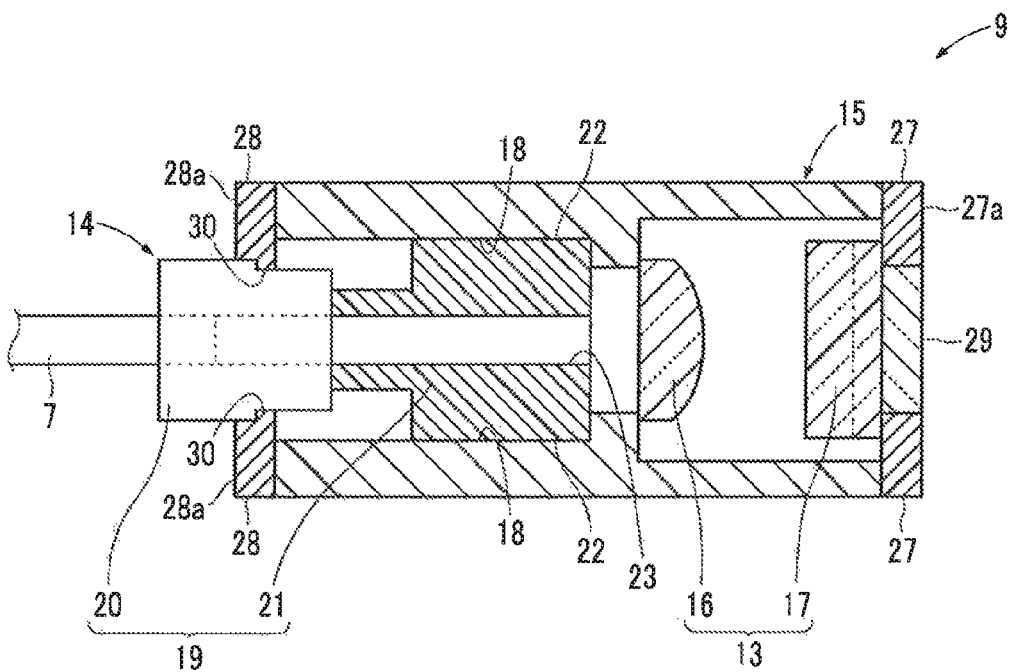
FIG. 2B is a side sectional view of the illumination portion.

FIG. 2A is a top sectional view of the illumination portion 9. FIG. 2B is a side sectional view of the illumination portion 9. As shown in FIGS. 2A and 2B, the illumination portion 9 includes: an illumination optical system 13 that forms the laser light from the optical fiber 7 into sheet-like illumination light 11 (see FIG. 1); a regulation portion 14 that regulates the focusing position of the laser light by the illumination optical system 13; and a housing 15 that houses the illumination optical system 13 and the regulation portion 14.

The illumination optical system 13 includes: a planoconvex cylindrical lens 16 that vertically focuses the laser light emitted from the end portion of the optical fiber 7; and a planoconcave cylindrical lens 17 that horizontally diverges the laser light focused by the planoconvex cylindrical lens 16. The planoconvex cylindrical lens 16 and the planoconcave cylindrical lens 17 are supported in the housing 15 so that their convex side and concave side face each other.

The regulation portion 14 includes a movable portion 19 that is movably guided in the optical axis direction of the illumination optical system 13 by a guide surface 18 of the inner surface of the housing 15. The movable portion 19 includes: a light introduction portion 20 that introduces the laser light from the optical fiber 7 into the illumination optical system 13; and a support portion 21 that supports the light introduction portion 20 with respect to the guide surface 18. The support portion 21 has a guide surface 22 corresponding to the guide surface 18.

The light introduction portion 20 is connected with the end portion of the optical fiber 7. The light introduction portion 20 and the support portion 21 have a through hole 23 concentric with the optical axis of the illumination optical system 13 so that the laser light emitted from the end portion of the optical fiber 7 enters into the illumination optical system 13 appropriately. The support portion 21 is provided with a female screw 24 whose center axis line is parallel to the optical axis of the illumination optical system 13. A male screw 25 is screwed with the female screw 24, as a drive screw for moving the movable portion 19 along the guide surfaces 18 and 22.

The outside shape of the housing 15 is substantially a quadrangular prism. The housing 15 includes: a body portion 26 having an internal space for containing the illumination optical system 13 and the movable portion 19; a front end plate 27 that blocks the space in which the illumination optical system 13 is contained; and a back end plate 28 that blocks the space in which the movable portion 19 is contained.

The front end plate 27 and the back end plate 28 each have substantially a rectangular flat plate shape that matches the shape of each end of the body portion 26. The outer plate surface of the front end plate 27 forms a front end surface 27a of the housing 15. The outer plate surface of the back end plate 28 forms a back end surface 28a of the housing 15.

The front end plate 27 is provided with a glass plate 29 as a rectangular transparent plate through which the laser light from the illumination optical system 13 passes. The front end surface 27a including the outer plate surface of the glass plate 29 is substantially a flat surface. In detail, the glass plate 29 in the front end surface 27a and the part of the front end surface 27a other than the glass plate 29 are coplanar with no difference in level. Alternatively, even if there is a difference in level, the part of the glass plate 29 protrudes from the part other than the glass plate 29, and the amount of protrusion is very small, for example, not greater than 0.1 mm.

The back end plate 28 has a through hole 30 whose diameter matches the outer periphery of the end of the light introduction portion 20 to which the optical fiber 7 is connected. The end of the light introduction portion 20 protrudes from the back end surface 28a through the through hole 30. This allows the end of the optical fiber 7 to be connected to the light introduction portion 20.

The back end plate 28 also has a through hole 31 through which the male screw 25 is inserted. The male screw 25 is inserted through the through hole 31 and screwed with the female screw 24 in the support portion 21, while pressing around the through hole 31 from outside with its head. A coil spring 32 that resists this pressing force is provided on the outer periphery of the male screw 25 between the inner side of the back end plate 28 and the support portion 21.

The position of the movable portion 19 in the optical axis direction can thus be regulated by operating the male screw 25. Accordingly, the distance between the end of the optical fiber 7 and the illumination optical system 13 can be changed to regulate the focusing position of the laser light by the illumination optical system 13.

Figure 3:
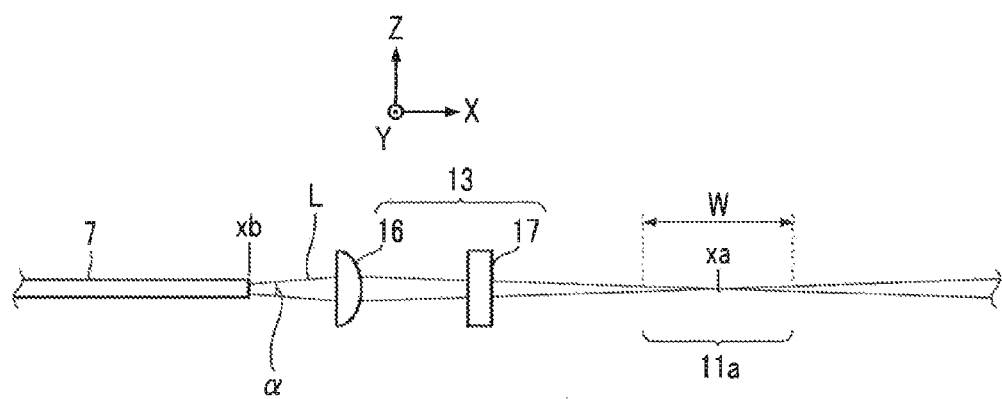
FIG. 3 is a view showing a situation where sheet-like illumination light is formed by an illumination optical system in the flow velocity measurement device in FIG. 1.

FIG. 3 shows a situation where sheet-like illumination light is formed by the illumination optical system 13. As shown in FIG. 3, the direction of emission of laser light L from the optical fiber 7 is X direction, the length direction of the planoconvex cylindrical lens 16 is Y direction, and the length direction of the planoconcave cylindrical lens 17 is Z direction. The laser light L emitted from the end portion of the optical fiber 7 is focused in Z direction (vertical direction) by the planoconvex cylindrical lens 16, and further diffused in Y direction (horizontal direction).

As a result, sheet-like illumination light 11 a suitable for illuminating the tracer particles, which spreads substantially in XY plane, is formed in a predetermined range W in X direction having a focusing position xa at its center. The two imaging portions 6 are set to image a fixed imaging area corresponding to this predetermined range W.

In the case where the output set value of the laser device 8 is changed, the spread angle α of the laser light L changes, too. Besides, in the case where a solid as a laser medium is changed in the laser device 8, the spread angle α and diameter of the laser light L change even when the model of the laser device 8 is unchanged. When the spread angle a increases, the focusing position xa changes. This change differs significantly depending on the type of the laser device 8 such as a solid-state laser or a carbon dioxide gas laser. Typically, however, when the output set value increases, the spread angle a increases, too. When the spread angle α increases, the focusing position xa becomes farther from the illumination optical system 13, and also the above described predetermined range W becomes farther from the illumination optical system 13.

The focusing position xa needs to be maintained at the appropriate position corresponding to the imaging area of the imaging portions 6, by operating the male screw 25 in the regulation portion 14 according to the change property of the spread angle α with respect to the change of the output set value of the laser device 8.

In detail, according to the above-mentioned change property, the male screw 25 in the regulation portion 14 is operated to set the position xb of the end of the optical fiber 7 to become farther from the illumination optical system 13 when the output set value is increased and closer to the illumination optical system 13 when the output set value is decreased.

The flow velocity measurement device 1 with this structure measures the flow velocity distribution in the flow field F as follows. First, air is blown into the wind tunnel and the tracer particles are supplied, thus forming the flow field F in which the tracer particles move with the air in the wind tunnel.

Next, the probe portion 5 in the flow velocity measurement device 1 is placed in an area in the flow field F where the flow velocity distribution is to be measured. The placement is preferably performed so that the sheet surface of the sheet-like illumination light 11 radiated from the illumination portion 9 is parallel to the flow direction 33 of the air in the flow field F. The placement can be performed by an operator, or a robot taught about the measurement area.

Next, the laser device 8 supplies the laser light to the illumination portion 9 in the probe portion 5, via the optical fiber 7. The illumination portion 9 accordingly radiates the sheet-like illumination light 11, as a result of which the tracer particles 12 in the radiation range are illuminated as shown in FIG. 1.

Simultaneously, the imaging portions 6 in the particle photographing device 2 image the illuminated tracer particles 12. The illumination and imaging is performed at two time points or more, with at least very short time intervals. Based on the imaging data of the tracer particles obtained at, the at least two time points or more in this way, the computer 3 calculates the flow velocity distribution in the imaging range. A publicly known method such as cross correlation or autocorrelation is used when calculating the flow velocity distribution. Such flow velocity distribution measurement can be performed in any area in the flow field F where the probe portion 5 in the particle photographing device 2 is placed.

In the case where the output of the laser device 8 is changed during the above operation, the position of the end of the optical fiber 7 is regulated by operating the male screw 25 in the regulation portion 14 in the above-mentioned manner according to need. The focusing position of the illumination light by the illumination portion 9 is thus maintained at the appropriate position with respect to the imaging area of the imaging portions 6.

There is also a possibility that the tracer particles in the flow field F adhere to the outer surface of the front end plate 27 in the illumination portion 9 during the above operation. However, since the outer surface of the front end plate 27 including the glass plate 29 is substantially one flat surface as mentioned above, even when the tracer particles adhere to the outer surface of the front end plate 27, the tracer particles are immediately blown away by the air pressure of the flow field F. Therefore, the defects caused by the tracer particles adhering to the glass plate 29, such as interfering with the passage of the illumination light 11 or unexpectedly refracting the illumination light 11, can be prevented.

As described above, according to this embodiment, the regulation portion 14 for regulating the focusing position of the laser light by the illumination optical system 13 by changing the position of the end of the optical fiber 7 is provided. The focusing position can thus be maintained at the appropriate position for the imaging area of the imaging portions 6. In this way, the illumination optical system 13 can be made more compact while ensuring that the tracer particles are photographed with high precision using a sufficient quantity of illumination light.

When the output set value of the laser device 8 is changed, the position of the end of the optical fiber 7 is changed by operating the male screw 25 in the regulation portion 14, to regulate the focusing position of the laser light by the illumination optical system 13. The position of illumination by the illumination portion 9 can thus be always maintained at the appropriate position.

The front end surface 27a of the housing 15 in the illumination portion 9, which includes the plate surface of the glass plate 29, forms one flat surface. Alternatively, even in the case where the plate surface of the glass plate 29 protrudes from the front end surface 27a, the amount of protrusion is very small. Therefore, the defects caused by the tracer particles adhering to the glass plate 29 can be prevented.

Both the head of the male screw 25 in the regulation portion 14 and the part of the movable portion 19 to which the optical fiber 7 is fixed protrude from the back end surface 28a of the housing 15. The oil of the tracer particles adhering to the front end surface 27a of the housing 15 is accordingly prevented from coming around to the head of the male screw 25 or to the part to which the optical fiber 7 is fixed, as much as possible. Hence, the male screw 25 and the optical fiber 7 can be prevented from stains and other adverse effects by the oil.

Figure 4:
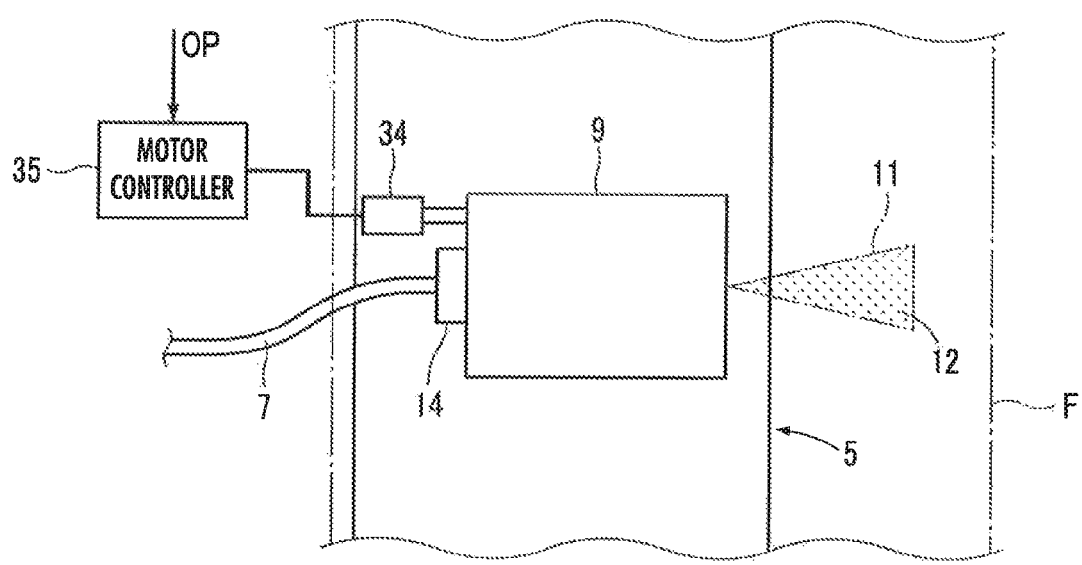
FIG. 4 is a top view of the vicinity of an illumination portion in a flow velocity measurement device according to another embodiment of the present invention.

FIG. 4 is a top view of the vicinity of the illumination portion 9 in a flow velocity measurement device according to another embodiment of the present invention. As shown in FIG. 4, the flow velocity measurement device includes: an encoder-equipped motor 34 connected to the male screw 25 in the illumination portion 9 described above; and a motor controller 35 that controls the motor 34.

The motor controller 35 may be realized by the computer 3. The motor controller 35 receives the output set value OP of the laser device 8. The other structure in this embodiment is the same as that in the embodiment shown in FIGS. 1 to 3. In this embodiment, the motor controller 35 regulates the position of the movable portion 19 in the optical axis direction by operating the male screw 25.

In detail, the motor controller 35 stores a correspondence table in which each possible output set value OP of the laser device 8 is associated with the amount of rotation of the motor 34. The amount of rotation of the motor 34 corresponding to the output set value OP is the amount of rotation of the motor 34 from its reference position that corresponds to the rotation position of the male screw 25 for setting the focusing position xa in FIG. 3 to the appropriate position corresponding to the imaging area of the imaging portions 6, at each output set value OP.

When the flow velocity measurement device 1 measures the flow velocity distribution in the flow field F, the motor controller 35 acquires the corresponding amount of rotation from the correspondence table based on the output set value OP of the laser device 8, and controls driving of the motor 34 based on the amount of rotation.

In this way, even in the case where the output set value OP is changed, the distance between the end of the optical fiber 7 and the illumination optical system 13 is changed appropriately. The focusing position xa of the laser light by the illumination optical system 13 is thus always maintained at the appropriate position corresponding to the imaging area of the imaging portions 6.

In the case where various types of laser device 8 are used or various types of laser medium are used in the laser device 8, the correspondence table may be provided for each type of laser device 8 or each type of laser medium.

The present invention is not limited to the embodiments described above. For example, the flow field F may be a flow field by a liquid. The tracer particles may be solid particles. Though the imaging portions 6 are included in the probe portion 5 in the embodiments described above, the imaging portions 6 may be provided at a position separate from the probe portion 5.

What is claimed is:

1. A particle photographing device comprising:
    a probe portion placed in a fluid in which particles are dispersed;
    an optical fiber that emits laser light from an end portion thereof; and
    an imaging portion that images the particles illuminated based on the laser light emitted from the end portion of the optical fiber,
    wherein the probe portion includes:
    an illumination optical system that illuminates the particles with sheet-like illumination light based on the laser light emitted from the end portion of the optical fiber; and
    a regulation portion that regulates a focusing position of the laser light by the illumination optical system, by changing a distance between the end portion of the optical fiber and the illumination optical system.

2. The particle photographing device according to claim 1, comprising
    a laser device that supplies the laser light introduced into the probe portion, to the optical fiber,
    wherein the regulation portion regulates the focusing position of the laser light by setting a position of the end portion of the optical fiber to become farther from the illumination optical system when an output set value of the laser light in the laser device is increased and to become closer to the illumination optical system when the output set value is decreased, to enable the illumination optical system to accurately illuminate an imaging range of the imaging portion regardless of a change of the output set value.

3. The particle photographing device according to claim 2, wherein the regulation portion includes:
    a motor that changes the distance between the end portion of the optical fiber and the illumination optical system; and
    a motor controller that controls the motor, and
    wherein the motor controller regulates the focusing position via the motor.

4. The particle photographing device according to claim 1, wherein the probe portion includes
    a housing that houses the illumination optical system,
    wherein the housing has a front end surface provided with a flat transparent plate through which the illumination light from the illumination optical system passes, and
    wherein an outer plate surface of the transparent plate in the front end surface and other part of the front end surface except the outer plate surface of the transparent plate are positioned coplanar, or the outer plate surface of the transparent plate protrudes from the other part and the protrusion amount is not greater than a predetermined value.

5. The particle photographing device according to claim 4, wherein the housing contains the regulation portion in a rear side of the illumination optical system, and has a back end surface at an opposite side of the front end surface,
    wherein the regulation portion includes:
    a movable portion to which the end portion of the optical fiber is fixed, and that is movably guided in an optical axis direction of the illumination optical system; and
    a drive screw that is screwed with the movable portion to change a position of the movable portion in the optical axis direction, and
    wherein a part of the movable portion to which the optical fiber is fixed and a head of the drive screw protrude from the back end surface.

6. A flow velocity measurement device comprising:
    the particle photographing device according to claim 1; and
    a computer that obtains a flow velocity distribution in a fluid, based on imaging data of tracer particles in the fluid obtained by the particle photographing device.

* * * * *